(12) United States Patent
Liu et al.

(10) Patent No.: US 11,793,712 B2
(45) Date of Patent: Oct. 24, 2023

(54) SYSTEM, APPARATUS, AND METHOD FOR CONTROLLING DEVICES USING AN ALARM

(71) Applicant: HYTTO PTE. LTD., Singapore (SG)

(72) Inventors: Dan Liu, Guangdong (CN); Jilin Qiu, Guangdong (CN)

(73) Assignee: HYTTO PTE. LTD., Singapore (SG)

( * ) Notice: Subject to any disclaimer, the term of this patent is extended or adjusted under 35 U.S.C. 154(b) by 0 days.

(21) Appl. No.: 17/835,632

(22) Filed: Jun. 8, 2022

(65) Prior Publication Data

US 2022/0296461 A1 Sep. 22, 2022

Related U.S. Application Data

(63) Continuation-in-part of application No. 17/717,917, filed on Apr. 11, 2022, and a continuation-in-part of application No. 17/579,839, filed on Jan. 20, 2022, and a continuation-in-part of application No. 16/835,808, filed on Mar. 31, 2020, now Pat. No. (Continued)

(51) Int. Cl.
*A61H 19/00* (2006.01)
*A61F 5/41* (2006.01)
*A61H 23/02* (2006.01)

(52) U.S. Cl.
CPC ............ *A61H 19/44* (2013.01); *A61F 5/41* (2013.01); *A61H 19/34* (2013.01); *A61F 2005/417* (2013.01); *A61H 23/02* (2013.01); *A61H 2201/5007* (2013.01); *A61H 2201/5071* (2013.01); *A61H 2201/5097* (2013.01)

(58) Field of Classification Search
CPC .......... A61H 1/00; A61H 19/34; A61H 19/44; A61H 2201/5007; A61H 19/30; A61H 2201/165; A61H 2201/501; A61H 2205/087
See application file for complete search history.

(56) References Cited

U.S. PATENT DOCUMENTS 3,361,130 A 1/1968 Rowe
5,807,287 A 9/1998 Cheng
(Continued)

FOREIGN PATENT DOCUMENTS

KR 101256565 B1 4/2013
WO 2006040750 A1 4/2006
WO 2008067487 A2 6/2008

*Primary Examiner* — Christine H Matthews
(74) *Attorney, Agent, or Firm* — McCarter & English, LLP; James M. Smedley; Alex Korona

(57) ABSTRACT

A system is disclosed. The system has an alarm control module, comprising computer-executable code stored in non-volatile memory, and an accessory including an accessory processor and an accessory memory. The alarm control module and the accessory are configured to control the accessory processor to execute on a first plurality of programming instructions stored by the accessory memory, the first plurality of programming instructions controlling the accessory and including one or more alarm clocks, and when the one or more alarm clocks that are preset in the accessory are activated, drive the accessory. Driving the accessory includes performing one or more predefined sexual stimulation acts to stimulate a human user of the accessory.

17 Claims, 8 Drawing Sheets

Related U.S. Application Data 11,452,669, which is a continuation of application No. 16/352,876, filed on Mar. 14, 2019, now Pat. No. 11,311,453.

(60) Provisional application No. 62/830,195, filed on Apr. 5, 2019.

(56) References Cited

U.S. PATENT DOCUMENTS

| | | |
|---|---|---|
| 6,277,085 B1 | 8/2001 | Flynn |
| 6,368,268 B1 | 4/2002 | Sandvick et al. |
| 8,255,299 B2 | 8/2012 | Cambridge |
| 8,644,967 B2 | 2/2014 | Seiler |
| 8,936,544 B2 | 1/2015 | Shahoian et al. |
| 9,762,515 B1 | 9/2017 | Olivares et al. |
| 10,051,328 B2 | 8/2018 | Olivares, II et al. |
| 10,218,795 B1 | 2/2019 | Messinger |
| 10,576,013 B1 | 3/2020 | Sloan |
| 11,134,041 B1 | 9/2021 | He |
| 2002/0065477 A1 | 5/2002 | Boyd et al. |
| 2002/0133103 A1 | 9/2002 | Williams et al. |
| 2003/0036678 A1 | 2/2003 | Abbassi |
| 2004/0082831 A1 | 4/2004 | Kobashikawa et al. |
| 2004/0097852 A1 | 5/2004 | Boyd et al. |
| 2005/0138560 A1 | 6/2005 | Lee et al. |
| 2006/0247561 A1 | 11/2006 | Chiu |
| 2012/0259171 A1 | 10/2012 | Shmakov |
| 2013/0165747 A1 | 6/2013 | Maggs |
| 2014/0011557 A1 | 1/2014 | Coyle |
| 2014/0115690 A1 | 4/2014 | Huang et al. |
| 2014/0276270 A1* | 9/2014 | Ludlow .............. A61N 5/0622 601/46 |
| 2016/0049043 A1 | 2/2016 | Tennenhaus et al. |
| 2017/0119619 A1 | 5/2017 | Dills |
| 2018/0116904 A1 | 5/2018 | Lieberman et al. |
| 2019/0133877 A1 | 5/2019 | Cambridge |
| 2020/0009009 A1 | 1/2020 | Nishida |
| 2020/0276504 A1 | 9/2020 | Liu |
| 2020/0289363 A1 | 9/2020 | Liu |
| 2020/0315908 A1 | 10/2020 | Liu |
| 2020/0366972 A1 | 11/2020 | Sloan |
| 2021/0341992 A1 | 11/2021 | Cambridge |
| 2022/0141550 A1 | 5/2022 | Liu |

\* cited by examiner

SYSTEM, APPARATUS, AND METHOD FOR CONTROLLING DEVICES USING AN ALARM

CROSS REFERENCE TO RELATED APPLICATIONS

This application is a continuation-in-part of U.S. patent application Ser. No. 17/579,839, filed Jan. 20, 2022. This application is also a continuation-in-part of U.S. patent application Ser. No. 17/717,917, filed Apr. 11, 2022, which is a continuation of U.S. patent application Ser. No. 16/352,876, filed Mar. 14, 2019 (now U.S. Pat. No. 11,311,453 issued on Apr. 26, 2022). This application is also a continuation-in-part of U.S. patent application Ser. No. 16/835,808, filed Mar. 31, 2020, which claims priority to U.S. Provisional Patent Application No. 62/830,195, filed Apr. 5, 2019. Each of the above applications is hereby incorporated by reference in its entirety.

FIELD OF THE INVENTION

The present disclosure generally relates to a system, apparatus, and method for controlling devices, and more particularly to a system, apparatus, and method for controlling devices using an alarm.

BACKGROUND OF THE INVENTION

Conventional techniques for controlling a device such as an adult toy using a schedule exist. Though conventional systems can activate a device immediately based on a schedule, such activation occurs when an application is in current use (at the front desk). However, when the application is not in current use (e.g., is in the background or nonactive), the user is typically notified of a scheduled activation by triggering the local system notification (provided that the user does not disable the remote notification function in a mobile phone system). Nevertheless, the device will not activate without users clicking the notification to open the application after receiving the notification from the local system. The above issues with conventional systems make the trigger conditions of scheduled activation ineffective, and difficult and burdensome to users.

In an attempt to address issues with scheduled activation, some systems have been modified to save data of scheduled activation in a device such as an adult toy instead of the application. However, this attempted solution has a natural defect. After an adult toy is turned off, data of scheduling information is lost. As a result, the device does not activate per the intended scheduled activation time. Also, data stored in such a device's firmware has minimal instruction data that can be executed, and cannot be executed according to a pattern set by the user in conventional systems. Typically, devices merely execute a monotonous vibration with certain fluctuation, and the instruction data originally stored in a toy cannot achieve a pattern or similar desirable operation criteria.

The exemplary disclosed system and method are directed to overcoming one or more of the shortcomings set forth above and/or other deficiencies in existing technology.

SUMMARY OF THE INVENTION

In one exemplary aspect, the present disclosure is directed to a system. The system includes an alarm control module, comprising computer-executable code stored in non-volatile memory, and an accessory including an accessory processor and an accessory memory. The alarm control module and the accessory are configured to control the accessory processor to execute on a first plurality of programming instructions stored by the accessory memory, the first plurality of programming instructions controlling the accessory and including one or more alarm clocks, and when the one or more alarm clocks that are preset in the accessory are activated, drive the accessory. Driving the accessory includes performing one or more predefined sexual stimulation acts to stimulate a human user of the accessory.

In another aspect, the present disclosure is directed to a method. The method includes providing a sexual stimulation device including an accessory processor and an accessory memory, controlling the accessory processor to execute on a first plurality of programming instructions stored by the accessory memory, providing a user device of a human user, the user device including a second processor and a second memory, and the user device communicably connected to the sexual stimulation device, and controlling the second processor to execute on a second plurality of programming instructions stored by the second memory. The method also includes presetting one or more alarm clocks in the user device, when the one or more alarm clocks activate, sending one or more control signals from the user device to the sexual stimulation device, and driving the sexual stimulation device, based on the one or more control signals, to perform one or more predefined sexual stimulation acts to stimulate the human user.

DETAILED DESCRIPTION AND INDUSTRIAL APPLICABILITY

Figure 1:
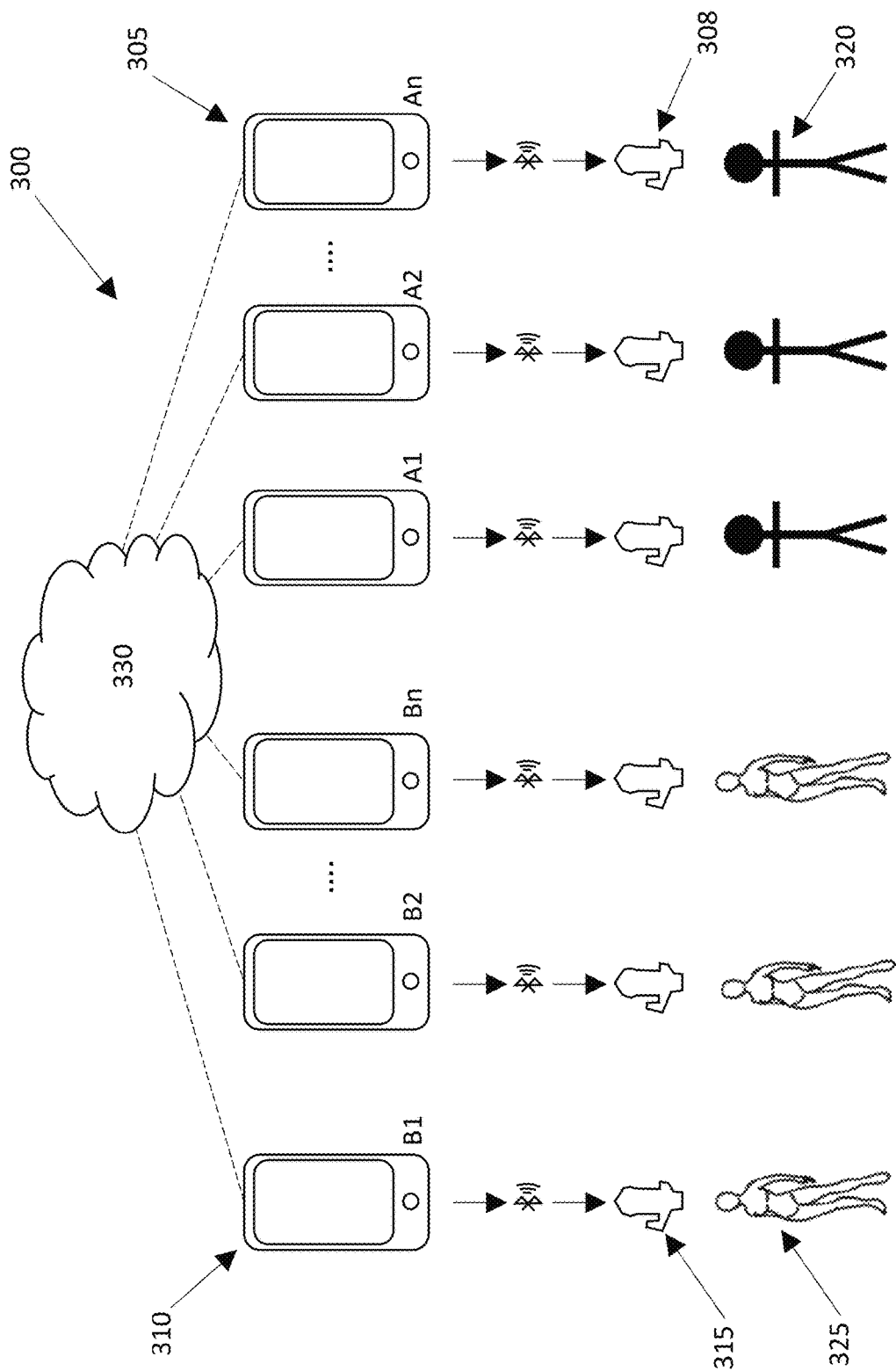
FIG. 1 is a schematic illustration of an exemplary system of the present invention.

FIG. 1 illustrates an exemplary system 300 for controlling devices using an alarm. In at least some exemplary embodiments, system 300 may be a system for controlling a sexual stimulation device, using an alarm, in real-time (e.g., in real-time or in near real-time) for an adult entertainment application.

As illustrated in FIG. 1, system 300 may include one or more user devices 305, one or more model devices 310, one or more viewer accessories 308, and one or more model accessories 315. For example, system 300 may include a plurality of user devices 305, a plurality of viewer accessories 308, a plurality of model devices 310, and a plurality of model accessories 315. Data such as image data, audio data, and/or control data may be transferred between user devices 305, viewer accessories 308, model devices 310, and model accessories 315.

As illustrated in FIG. 1, system 300 may include any desired number of user devices 305 (e.g., A1, A2, . . . An). User device 305 may be any suitable device for interfacing with other components of system 300 such as a computing device (e.g., user interface). For example, user device 305 may be any suitable user interface for receiving input and/or providing output (e.g., image data) to a user 320. User device 305 may include a camera and a microphone. User device 305 may be, for example, a touchscreen device (e.g., of a smartphone, a tablet, a smartboard, and/or any suitable computer device), a wearable device, a computer keyboard and monitor (e.g., desktop or laptop), an audio-based device for entering input and/or receiving output via sound, a tactile-based device for entering input and receiving output based on touch or feel, a dedicated user interface designed to work specifically with other components of system 300, and/or any other suitable user interface (e.g., including components and/or configured to work with components described below regarding FIGS. 6 and 7). For example, user device 305 may include a touchscreen device of a smartphone or handheld tablet. For example, user device 305 may include a display (e.g., a computing device display, a touchscreen display, and/or any other suitable type of display) that may provide output, image data, and/or any other desired output or input prompt to a user. For example, the exemplary display may include a graphical user interface to facilitate entry of input by a user and/or receiving output such as image data. An application for example as described herein and/or a web browser may be installed on user device 305 and utilized by user 320. User device 305 may include storage for example as described regarding FIG. 6. For example, user device 305 may have storage for storing programming instructions for example as described below.

Figure 2:
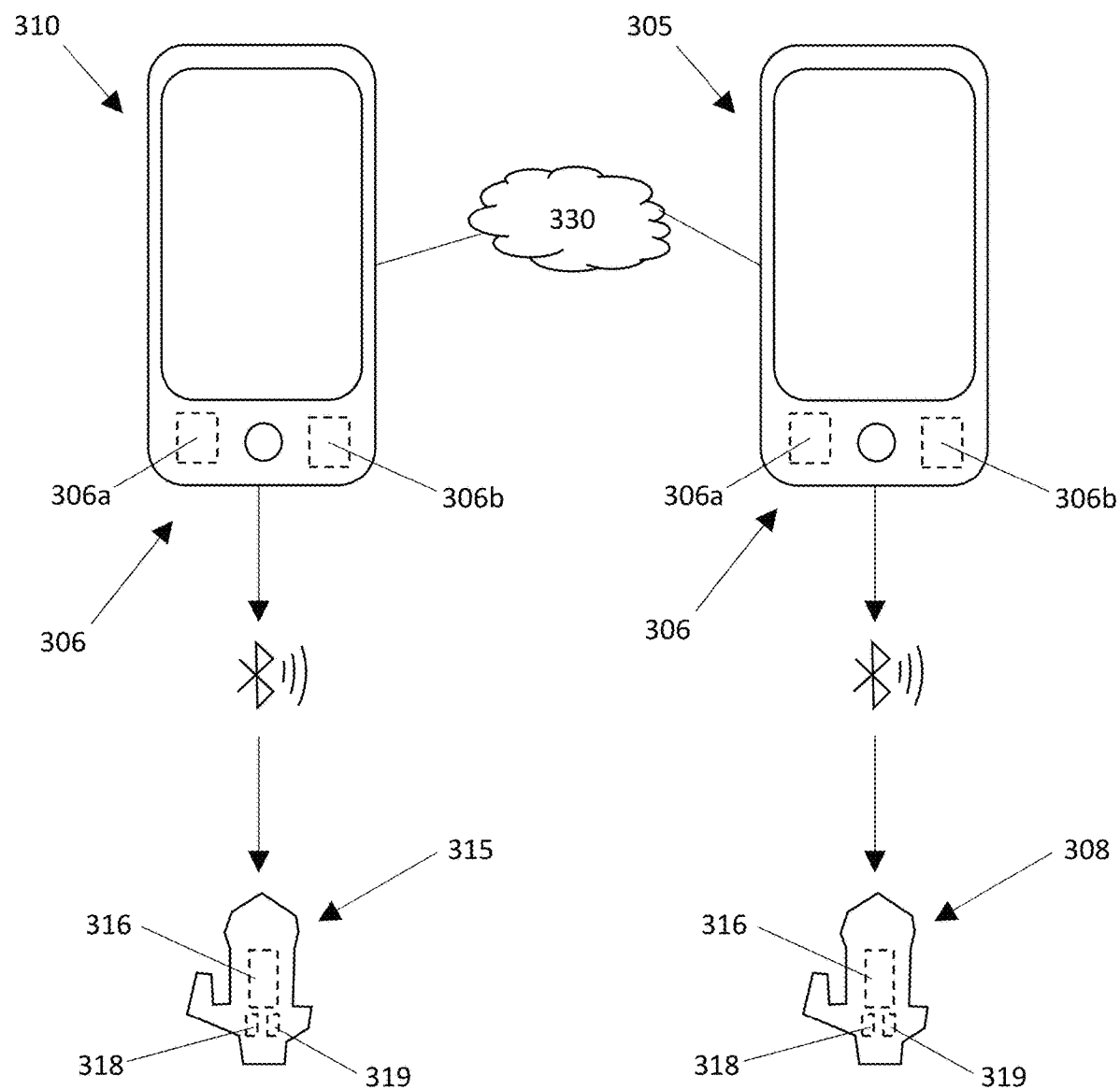
FIG. 2 is a schematic illustration of an exemplary system of the present invention.

As illustrated in FIG. 2, user device 305 may include a sensor array 306. In at least some exemplary embodiments, sensor array 306 may include one or more sensors integrated or built into the exemplary disclosed user device (e.g., user device 305) such as, for example, a mobile phone, a pad, or a wearable device. Sensor array 306 may include any suitable sensors for use with system 300 such as, for example, a location sensor 306*a* and a movement sensor 306*b*. Location sensor 306*a* may include a GPS device, a Galileo device, a GLONASS device, an IRNSS device, a BeiDou device, and/or any other suitable device that may operate with a global navigation system.

Movement sensor 306*b* may include any suitable components for sensing motion (e.g., motion amplitude), velocity, and/or acceleration. Movement sensor 306*b* may include an acceleration sensor. Movement sensor 306*b* may include a gyroscope. For example, movement sensor 306*b* may include a displacement sensor, a velocity sensor, and/or an accelerometer. For example, movement sensor 306*b* may include components such as a servo accelerometer, a piezoelectric accelerometer, a potentiometric accelerometer, and/or a strain gauge accelerometer. Movement sensor 306*b* may include a piezoelectric velocity sensor or any other suitable type of velocity or acceleration sensor.

System 300 may include any desired number of model devices 310 (e.g., B1, B2, . . . Bn). Model device 310 may be similar to user device 305. For example, model device 310 may be any suitable user interface for receiving input and/or providing output (e.g., image data) to a model 325. Model 325 (e.g., a specific user) may operate model device 310 (e.g., a specific user device) to record and transfer image (e.g., video) and audio data to one or more users 320 via a network 330.

Model accessory 315 may be any suitable accessory for use by model 325 (e.g., when model 325 is imaged by model device 310). For example, model accessory 315 may be a prop that is used by model 325 while model 325 is being imaged (e.g., a video or pictures of model 325 are being recorded and/or transmitted in real-time to be viewed by user 320). For example, model accessory 315 may be a device used for erotic stimulation (e.g., a sex aid or a "sex toy"). Model accessory 315 may be a sexual simulation device that may be associated with a given model 325 (e.g., a specific user) and respective model device 310 (e.g., a specific user device) of that given model 325. In at least some exemplary embodiments, model accessory 315 may be a massaging apparatus for human genitalia (e.g., a vibrator). For example, model accessory 315 may be any suitable device for use in a video or pictures recorded by model device 310, which may be an erotic video or erotic pictures). In at least some exemplary embodiments, model accessory 315 may be a tool or other indicator that may be used in video or pictures recorded by model device 310 such as surveying equipment, a sign providing information such as location or time information, a surveillance tool used by model 325, and/or any other suitable tool or accessory that may be used while model device 310 is recording a video or pictures of model 325. For example, model 325 may be an erotic model using model accessory 315 that may be an erotic device, a technician or laborer using model accessory 315 that may be a tool or work device specific to a desired application, an operative using model accessory 315 that may be a surveillance tool or a part of a weapon system being recorded by model device 310, and/or any other desired role using any suitable model accessory 315.

Model accessory 315 may include a motor 316. Motor 316 may include an electric motor. Motor 316 may include a server motor, a stepper motor, a brushless motor, or any other suitable type of motor. Motor 316 may include any suitable vibration motor or haptic motor such as, for example, a mini vibrator motor. Motor 316 may include a low voltage motor. Motor 316 may include a pager motor or a coin vibration motor. Motor 316 may include a linear resonant actuator or an eccentric rotating mass vibration motor. Motor 316 may be powered by any suitable power source, such as a battery (e.g., a nickel-metal hydride battery, a lithium-ion battery, an ultracapacitor battery, a lead-acid battery, and/or a nickel cadmium battery), an electric power source (e.g., a transformer connected to a plug that may plug into an outlet), and/or any other suitable energy source. Model accessory 315 may include a controller 319 that may be any suitable computing device for controlling an operation of motor 316 and a communication device 318. Controller 319 may, for example, include components similar to the components described below regarding FIG. 6. Controller 319 may include for example a processor (e.g., micro-processing logic control device) or board components. Controller 319 may control motor 316 based on input data and/or commands received from user device 305 and/or model device 310 via network 330 and/or a communication device 318 (e.g., transferred directly to communication device 318 by any suitable component of system 300). Motor 316 may be controlled by controller 319 to vibrate model accessory 315 at a desired level or strength, perform a suction operation at a desired level or strength using model accessory 315 (e.g., using model accessory 315 as a suction device), rotate or swing model accessory 315 at a desired speed or amount, contract or expand model accessory 315 by a desired amount, cause model accessory 315 to perform an inhalation action, and/or cause model accessory 315 to perform any other suitable action or function. Controller 319 may include storage for example as described regarding FIG. 6. For example, controller 319 may have storage for storing programming instructions for example as described below.

In at least some exemplary embodiments, motor 316 may be or may include a thermal device such as a heater. In at least some exemplary embodiments, motor 316 may include an electric heating device such as an electric resistance heating device. Motor 316 may include a polyimide heater, a silicone rubber heater, and/or a resistive wire heater. Motor 316 may be controlled by controller 319 to heat or emit heat or warmth from model accessory 315. For example, motor 316 may cause a temperature variation of model accessory 315.

Viewer accessory 308 may be similar to model accessory 315. Viewer accessory 308 may be a sexual simulation device that may be associated with a given user 320 (e.g., a viewer of one or more models 325) and respective user device 305 (e.g., a viewer device) of that given user 320.

Network 330 may be any suitable communication network over which data may be transferred between one or more user devices 305, one or more viewer accessories 308, one or more model devices 310, and/or one or more model accessories 315. Network 330 may be the internet, a LAN (e.g., via Ethernet LAN), a WAN, a WiFi network, or any other suitable network. Network 330 may be similar to WAN 201 described below. The components of system 300 may also be directly connected (e.g., by wire, cable, USB connection, and/or any other suitable electro-mechanical connection) to each other and/or connected via network 330. For example, components of system 300 may wirelessly transmit data by any suitable technique such as, e.g., wirelessly transmitting data via 4G LTE networks (e.g., or 5G networks) or any other suitable data transmission technique for example via network communication. Components of system 300 may transfer data via the exemplary techniques described below regarding FIG. 7. User devices 305, viewer accessories 308, model devices 310, and/or model accessories 315 may include any suitable communication components for communicating with other components of system 300 using for example the communication techniques described above. For example, user devices 305 and model devices 310 may include integrally formed communication devices (e.g., smartphone components), and viewer accessories 308 and model accessories 315 may each include communication device 318 that may communicate using any of the exemplary disclosed communication techniques.

In at least some exemplary embodiments, a given model accessory 315 may communicate with a given model device 310 (e.g., a paired model device 310) via any suitable short distance communication technique. For example, model accessories 315 (e.g., via communication device 318) and model devices 310 may communicate via WiFi, Bluetooth, ZigBee, NFC, IrDA, and/or any other suitable short distance technique. Model accessory 315 may be an adult toy that may be connected with model device 310 through short distance wireless communication. An application (e.g., operating using the exemplary disclosed modules) may be installed on model device 310, the application and model device 310 being configured to send commands to model accessory 315 to drive (e.g., actuate) model accessory 315. Viewer accessory 308 may communicate with user device 305 similarly to the communication of model accessory 315 and model device 310 described above.

System 300 may include one or modules for performing the exemplary disclosed operations. The one or more modules may include an accessory control module for controlling viewer accessory 308 and model accessory 315. The one or more modules may be stored and operated by any suitable components of system 300 (e.g., including processor components) such as, for example, network 330, user device 305, viewer accessory 308, model device 310, model accessory 315, and/or any other suitable component of system 300. For example, system 300 may include one or more modules having computer-executable code stored in non-volatile memory. System 300 may also include one or more storages (e.g., buffer storages) that may include components similar to the exemplary disclosed computing device and network components described below regarding FIGS. 6 and 7. For example, the exemplary disclosed buffer storage may include components similar to the exemplary storage medium and RAM described below regarding FIG. 6. The exemplary disclosed buffer storage may be implemented in software and/or a fixed memory location in hardware of system 300. The exemplary disclosed buffer storage (e.g., a data buffer) may store data temporarily during an operation of system 300.

Figure 3:
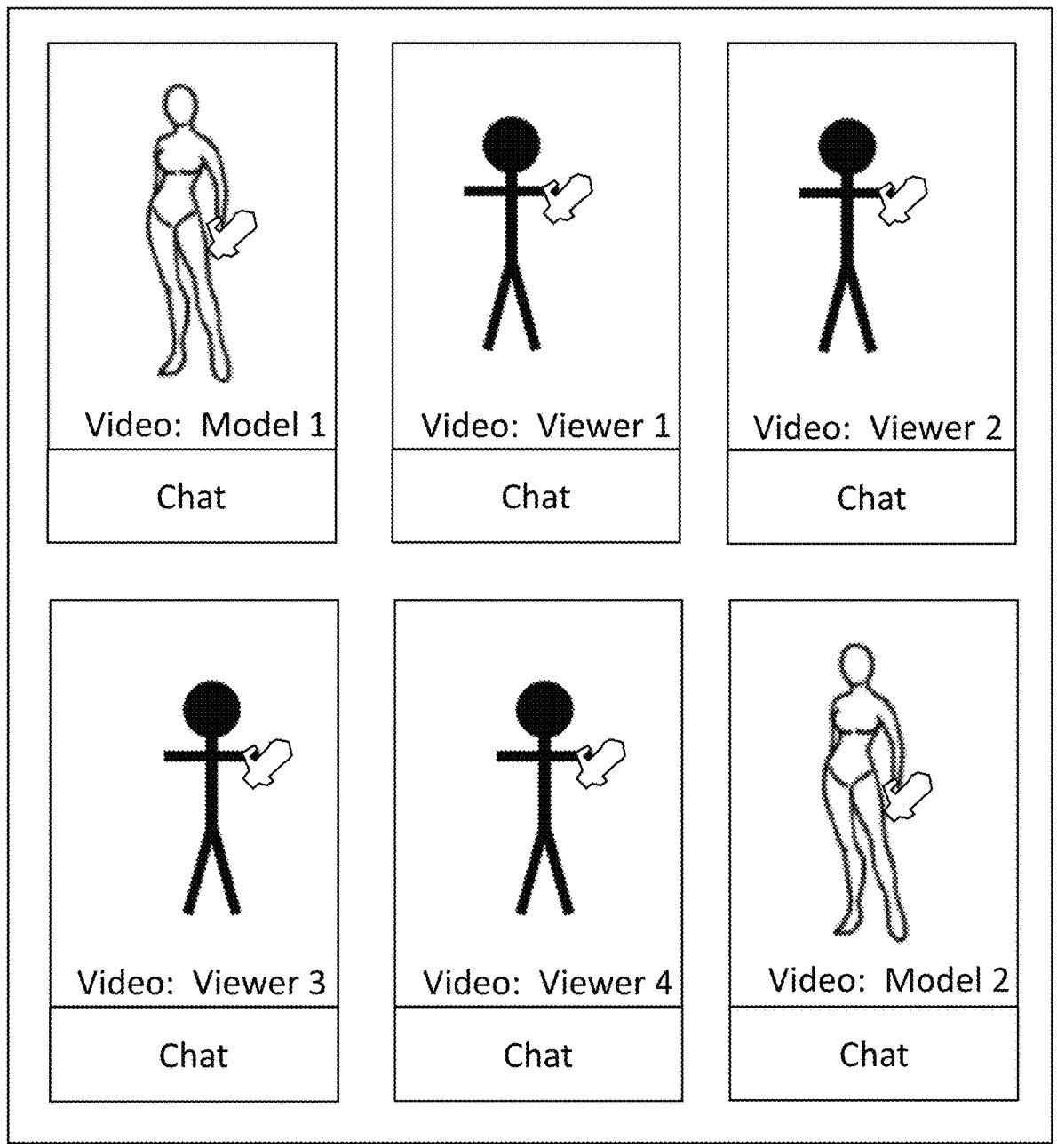
FIG. 3 is a schematic illustration of an exemplary system of the present invention.

The one or more exemplary disclosed modules may also provide a chat room interface via user device 305 and model device 310 for use by each user 320 and model 325. For example, video display of model 325, one or more users 320, and/or and a chat or messaging app (e.g., any suitable chat communication or messaging app such as, for example, text, voice, and/or video chat boxes) may be displayed to each user 320 via user device 305 and to each model 325 via model device 310. One or more users 320 and one or more models 325 may thereby view and chat (e.g., text, voice, and/or video chat) with each other via the one or more exemplary disclosed modules via respective user devices 305 and model devices 310. Each user 320 may thereby view, interact with, and/or chat (e.g., text, voice, and/or video chat) with one or more models 325 and/or other users 320. Also, each model 325 may thereby view, interact with, and/or chat with one or users 320 and/or other models 325. For example, multiple text, voice, and/or video chat boxes including a plurality of users 320 (e.g., viewers each having one or more viewer accessories 308) and/or a plurality of models 325 (e.g., each having one or more model accessories 315) may be displayed to each user 320 and each model 325 via respective user devices 305 and model devices 310. Users 320 and models 325 may thereby view and interact with other users 320 and models 325 that may each have one or more respective accessories (e.g., respective viewer accessories 308 and model accessories 315). FIG. 3 schematically illustrates an exemplary embodiment of the exemplary disclosed chat room that may be displayed to user 320 via user device 305 or to model 325 via model device 310.

The exemplary disclosed system, apparatus, and method may be used in any suitable telecommunications application. The exemplary disclosed system, apparatus, and method may be used in any suitable application for controlling a device based on an alarm. The exemplary disclosed system, apparatus, and method may be used in any suitable application for controlling a device according to a schedule (e.g., desired activation schedule). The exemplary disclosed system, apparatus, and method may be used in any suitable application for controlling a device such as an adult toy. The exemplary disclosed system, apparatus, and method may be used in any suitable telecommunication application for adult entertainment.

Figure 4:
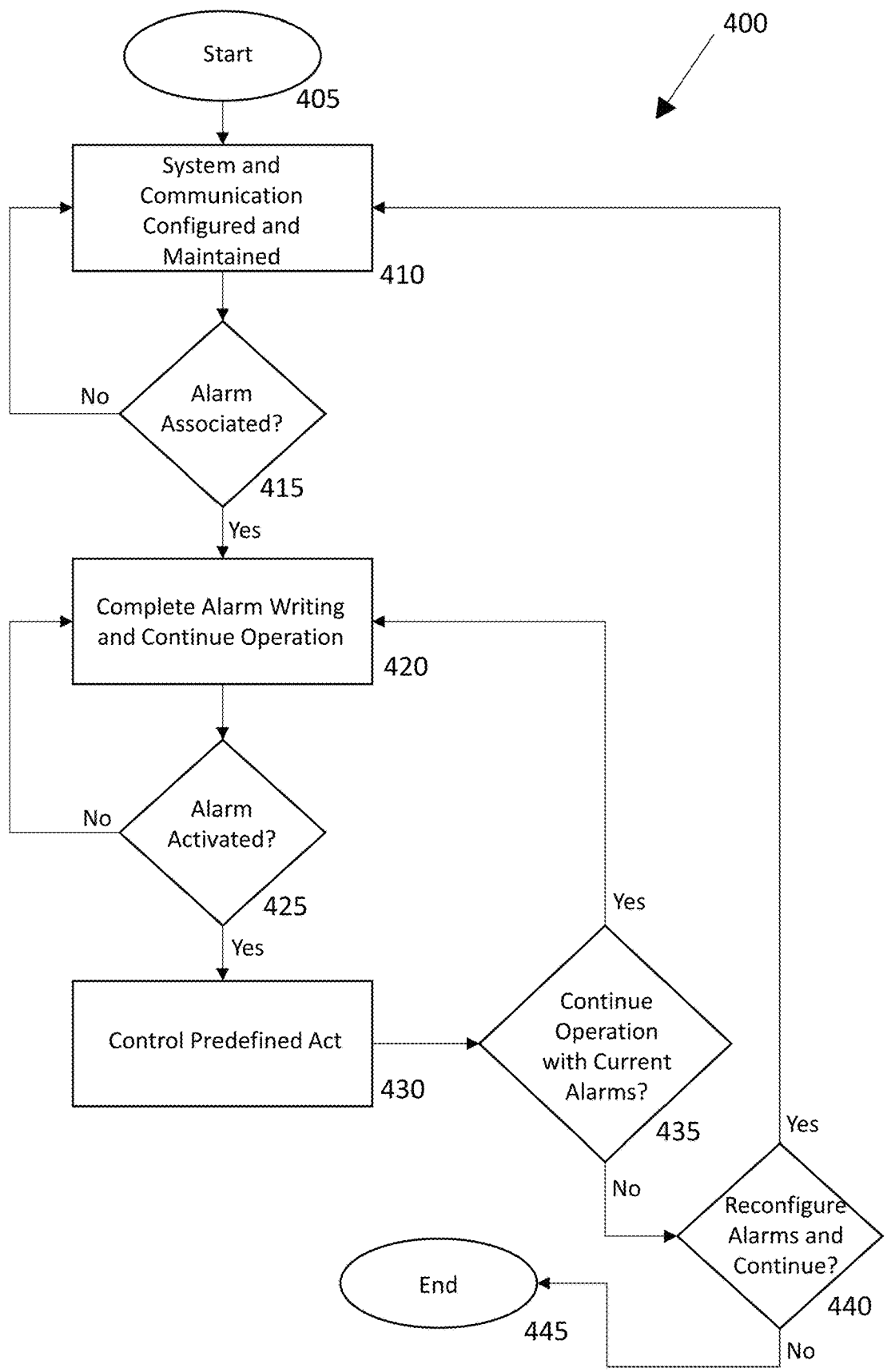
FIG. 4 is a flowchart showing an exemplary process of the present invention.

An exemplary operation of the exemplary disclosed system, apparatus, and method will now be described. FIG. 4 illustrates an exemplary process 400 of system 300. Process 400 begins at step 405.

At step 410, system 300 may be configured, re-configured, and/or communication provided by system 300 may be maintained. For example, system 300 may be configured as illustrated in FIGS. 1 and 2 or with any other suitable configuration. System 300 may provide a communication interface such as a chat room or interactive application to one or more users 320 and/or one or more models 325 such as, for example, as illustrated in FIG. 3. One or more users 320 and one or more models 325 may thereby communicate and interact with each other using live video communication in real-time or near real-time. Any desired number and arrangement of user devices 305, viewer accessories 308, model devices 310, and model accessories 315 may be included in the configuration of system 300. One or more viewer accessories 308 and one or more model accessories 315 (e.g., sexual stimulation devices such as operable adult toys) may be configured to receive data and signals from other components of system 300 for example as described herein. The exemplary disclosed module, storage (e.g., storage buffer), and hardware may include a memory having stored thereon instructions, a processor configured to execute the instructions resulting in a software application, and a software application configured to perform process 400.

In at least some exemplary embodiments at step 410, user 320 may install an application of system 300 (e.g., including programming instructions) on user device 305 and/or controller 319 (e.g., and/or model 325 may install the application on model device 310 and/or controller 319). For example, controller 319 (e.g., of viewer accessory 308 and/or model accessory 315) may store a first plurality of programming instructions, and user device 305 and/or model accessory 315 may store a second plurality of programming instructions for example as described herein. User 320 (e.g., and/or model 325) may authorize the application to access and control functions of user device 305, viewer accessory 308, model device 310, and/or model accessory 315. User 320 (e.g., and/or model 325) may also authorize the application to access the data of Bluetooth or any other suitable communication components of user device 305 (e.g., and/or model device 310). Model 325 (e.g., and/or user 320) may also connect model accessory 315 (e.g., and/or viewer accessory 308) to model device 310 (e.g., and/or user device 305) via Bluetooth or any other suitable communication technique. In at least some exemplary embodiments, viewer accessory 308 and/or model accessory 315 may be connected by the exemplary disclosed short range communication techniques to user device 305 and/or model device 310 and operated by user 320 and/or model 325 (e.g., user 320 and/or model 325 may control any of the exemplary disclosed devices directly or via network 330).

Controller 319 (e.g., of viewer accessory 308 and/or model accessory 315) may store the first plurality of programming instructions that may include data and/or signals associated with one or more alarm clocks (e.g., alarm clock functions). The data of the one or more alarm clocks may provide for writing into (e.g., writing or transferring data to) viewer accessory 308 (e.g., and/or model accessory 315) from user device 305 (e.g., and/or model accessory 315). For example, data of the second plurality of programming instructions of user device 305 (e.g., and/or model accessory 315) may be used to write into controller 319 (e.g., of viewer accessory 308 and/or model accessory 315). For example, the second plurality of programming instructions may include data of one or more alarm clock information, wherein the one or more alarm clock information may include one or more alarm clocks (e.g., associated with the one or more alarm clocks of the first plurality of programming instructions) for writing into the exemplary disclosed sexual stimulation device (e.g., controller 319 of viewer accessory 308 and/or model accessory 315) from the exemplary disclosed control device (e.g. user device 305 and/or model accessory 315).

At step 415, system 300 may determine whether or not alarm data of the first plurality of programming instructions and the second plurality of programming instructions are associated with each other. For example, system 300 may complete alarm writing data if the first plurality of programming instructions and the second plurality of programming instructions are associated, for example as described herein. For example, system 300 may transfer query data to controller 319 (e.g., of viewer accessory 308 and/or model accessory 315), user device 305, and/or model accessory 315 to determine whether or not alarm data of the first plurality of programming instructions and the second plurality of programming instructions are associated. If alarm data is not present and/or alarm data of the first plurality of programming instructions and the second plurality of programming instructions are not associated, process 400 may return to step 410. If system 300 determines that alarm data of the first plurality of programming instructions and the second plurality of programming instructions are associated, process 400 may proceed to step 420.

At step 420, system 300 may complete writing of alarm data using alarm data and/or signals associated with the first plurality of programming instructions of controller 319 (e.g., of viewer accessory 308 and/or model accessory 315) and the second plurality of programming instructions of user device 305 (e.g., and/or model accessory 315). For example, system 300 may send data and/or signals associated with one or more alarm clock information of the second plurality of programming instructions of user device 305 (e.g., and/or model accessory 315) to controller 319 (e.g., of viewer accessory 308 and/or model accessory 315) having the first plurality of programming instructions, which may complete an alarm writing setting of viewer accessory 308 and/or model accessory 315. For example, user device 305 (e.g., and/or model accessory 315) may complete the alarm writing setting (e.g., or settings) of viewer accessory 308 (and/or model accessory 315) to which that user device 305 is connected.

At step 425, system 300 may determine whether an alarm clock is activated. For example, system 300 may determine whether or not one or more alarm clocks of the first plurality of programming instructions of controller 319 (e.g., of viewer accessory 308 and/or model accessory 315) has been activated based on the alarm writing setting (e.g., or settings) completed at step 420. If one or more alarm clocks has not been activated, process 400 may return to step 420. If one or more alarm clocks has been activated, process 400 may proceed to step 430.

At step 430, system 300 may control the exemplary disclosed device (e.g., one or more viewer accessories 308 and/or model accessories 315) to perform a predefined act. The predefined act may be a predefined sexual stimulation act to stimulate a human user. The predefined act may include any desired operation of viewer accessory 308 and/or model accessory 315. For example, a predefined act of viewer accessory 308 and/or model accessory 315 may include vibration, a suction operation, rotation, swinging, contracting, expanding, performing an inhalation action, heating, cooling, undergoing temperature variation, and/or any other suitable action or function for example as described herein. The predefined act may be a predetermined act, based on user input (e.g., of one or more users 320 and/or one or more models 325), an algorithm of the exemplary disclosed module, a machine learning operation of the exemplary disclosed system, and/or any other suitable criteria for determining a predefined act. The predefined act may include one or more control patterns for controlling one or more viewer accessories 308 and/or model accessories 315 for example as described herein.

In at least some exemplary embodiments, when one or more alarm clocks (e.g., based on data of the first plurality of programming instructions) preset in of viewer accessory 308 and/or model accessory 315 (e.g., a sexual stimulation device) are activated (e.g., go off), viewer accessory 308 and/or model accessory 315 may be actuated to perform one or more exemplary predefined acts such as predefined sexual stimulation acts to stimulate an operator of the exemplary disclosed device (e.g., user 320 and/or model 325).

The exemplary disclosed alarm clock information (e.g., of data and/or signals associated with the second plurality of programming instructions) may include drive signals for said predefined sexual stimulation act associated with each alarm clock associated with the first plurality of programming instructions. The drive signals of the predefined act (e.g., predefined sexual stimulation act) may include the duration of the act, the amplitude of the act, the frequency of the act, and/or the intensity of the act when the predefined sexual stimulation act is performed. The exemplary disclosed alarm clock information may include a ring duration of the alarm clock, a number of alarm iterations (e.g., repeats), and/or an interval time of an alarm loop of the alarm clock.

In at least some exemplary embodiments, when user device 305 (e.g., or model device 310) is disconnected from viewer accessory 308 (e.g., or model accessory 315), the first plurality of programming instructions may be used to cause viewer accessory 308 (e.g., or model accessory 315) to operate (e.g., control an operation of the exemplary disclosed sexual stimulation device). For example when the written (e.g., based on step 420) one or more alarm clocks activate (e.g., sound), viewer accessory 308 (e.g., or model accessory 315) may execute one or more of the predefined acts such as predefined sexual stimulation acts based on the exemplary disclosed drive signals associated with each of the alarm clocks of the first plurality of programming instructions. The operator (e.g., user 320 or model 325) of the sexual stimulation device may thereby be stimulated.

In at least some exemplary embodiments, the alarm clock information of the second plurality of programming instructions may include (e.g., and/or be associated with) one or more local alarm clocks that may be preset in the exemplary disclosed control device (e.g., user device 305 and/or model device 310). The one or more local alarm clocks of the second plurality of programming instructions may correspond to one or more alarm clocks (e.g., of the first plurality of programming instructions) written into the exemplary disclosed sexual stimulation device (e.g., viewer accessory 308 and/or model accessory 315). The second plurality of programming instructions may be configured to control the exemplary disclosed control device (e.g., user device 305 and/or model device 310) to perform the exemplary disclosed predefined act. Data and/or signals associated with the second plurality of programming instructions may provide (e.g., set) correspondence between the one or more local alarm clocks (e.g., of the second plurality of programming instructions) and the one or more alarm clocks (e.g., of the first plurality of programming instructions) written into the exemplary disclosed sexual stimulation device (e.g., viewer accessory 308 and/or model accessory 315). Data and/or signals associated with the second plurality of programming instructions may provide (e.g., set) associated one or more control patterns for each of the exemplary disclosed local alarm clocks associated with the second plurality of programming instructions. The exemplary disclosed control patterns may include a series of signals for driving the exemplary disclosed sexual stimulation device (e.g., viewer accessory 308 and/or model accessory 315) to perform continuously different amplitudes, continuously different frequencies, and/or different intensities of the exemplary disclosed predefined act (e.g., predefined sexual stimulation act).

In at least some exemplary embodiments, when the exemplary disclosed control device (e.g., user device 305 and/or model device 310) is connected with the exemplary disclosed sexual stimulation device (e.g., viewer accessory 308 and/or model accessory 315), the first plurality of programming instructions and the second plurality of programming instructions may be configured to send a plurality (e.g., a series) of signals corresponding to one or more exemplary disclosed control patterns to the exemplary disclosed sexual stimulation device when one or more local alarm clocks (e.g., associated with the second plurality of programming instructions) of the exemplary disclosed control device (e.g., user device 305 and/or model device 310) are activated (e.g., go off). The exemplary disclosed sexual stimulation device (e.g., viewer accessory 308 and/or model accessory 315) may receive the series of signals corresponding to one or more exemplary disclosed control patterns and may drive the exemplary disclosed sexual stimulation device to perform continuously different amplitudes, continuously different frequencies, and/or different intensities of the exemplary disclosed defined act (e.g., predefined sexual stimulation act).

At step 435, system 300 may determine whether or not an operation is to be continued with the current alarm settings. The determination may be based on predetermined criteria, user input (e.g., of one or more users 320 and/or one or more models 325), an algorithm of the exemplary disclosed module, a machine learning operation of the exemplary disclosed system, and/or any other suitable criteria for making the determination. If operation is to be continued with the current alarm settings, process 400 may return to step 420. If operation is not to be continued with the current alarm settings, process 400 may proceed to step 440.

At step 440, system 300 may determine whether or not the alarms are to be reconfigured and an operation is to be continued. The determination may be based on predetermined criteria, user input (e.g., of one or more users 320 and/or one or more models 325), an algorithm of the exemplary disclosed module, a machine learning operation of the exemplary disclosed system, and/or any other suitable criteria for making the determination. If the alarms are to be reconfigured and an operation is to be continued, process 400 may return to step 410. If the alarms are not to be reconfigured and an operation is not to be continued, process 400 may end at step 445.

In at least some exemplary embodiments, system 300 may be configured (e.g., the exemplary disclosed one or more modules may be configured) to define (e.g., set up or to have) one or more ranges of rewards or tips for example for models 325. Each of the one or more ranges of rewards or tips may correspond to a given predefined act. Rewards or tips may include virtual currency that may be purchased by (e.g., user 320) or credited to (e.g., model 325) users using any suitable payment technique. Rewards or tips may be awarded by user 320 to model 325 based on a performance of model 325 viewed by user 320 (e.g., adult entertainment). In at least some exemplary embodiments, each user 320 may provide tips via the user's user device 305, and each model 325 may receive tips via the model's model device 310.

In at least some exemplary embodiments, the exemplary disclosed system may be an operable sexual stimulation device configured to receive signals, including a memory, and a processor. The processor may execute on a first plurality of programming instructions stored on the memory, the first plurality of programming instructions controlling the sexual stimulation device. The system may also include a control device. The control device may be connected to the sexual stimulation device via short-range wireless. The control device may include a memory and a processor. The processor may execute on a second plurality of programming instructions stored on the memory, the second plurality of programming instructions controlling the control device. The first plurality of programming instructions, the second plurality of programming instructions, the sexual stimulation device, and the control device may be configured to operate with one or more alarm clocks that may be preset in the control device. When the one or more alarm clocks go off, one or more control signals may be sent to the sexual stimulation device, which may actuate the sexual stimulation device to perform one or more predefined sexual stimulation acts and to stimulate an operator of the sexual stimulation device.

In at least some exemplary embodiments, the exemplary disclosed system and method may include one or more alarm clocks (e.g., alarm clock functions). The alarm clock function may provide for the exemplary disclosed accessory such as an adult toy to vibrate regularly. A user (e.g., user 320 and/or model 325) may set their own alarm clock and/or accept an alarm clock sent by other users (e.g., friends) using system 300. When an alarm is activated, the system may trigger a command to the connected toy to vibrate the toy for example as described herein. The exemplary disclosed system and method may thereby achieve a rhythmic vibration effect.

In at least some exemplary embodiments, the exemplary disclosed alarm clock (e.g., alarm clock function) may include a snooze function that may provide for a desired number of executions or repetitions (e.g., planned or scheduled iterations). For example, the alarm clock may repeat at desired time intervals (e.g., every desired amount of minutes or hours) and/or operate for desired periods of time. For example, the snooze function may have parameters such as a snooze count (e.g., a number of times the alarm clock repeats) and/or a snooze duration (e.g., an alarm clock repetition interval). The system and/or a user may thereby control an amount of times the alarm clock repeats and/or after how many minutes or hours the alarm clock repeats. For example, the user and/or the system may set a playback duration of the alarm clock.

Figure 5A:
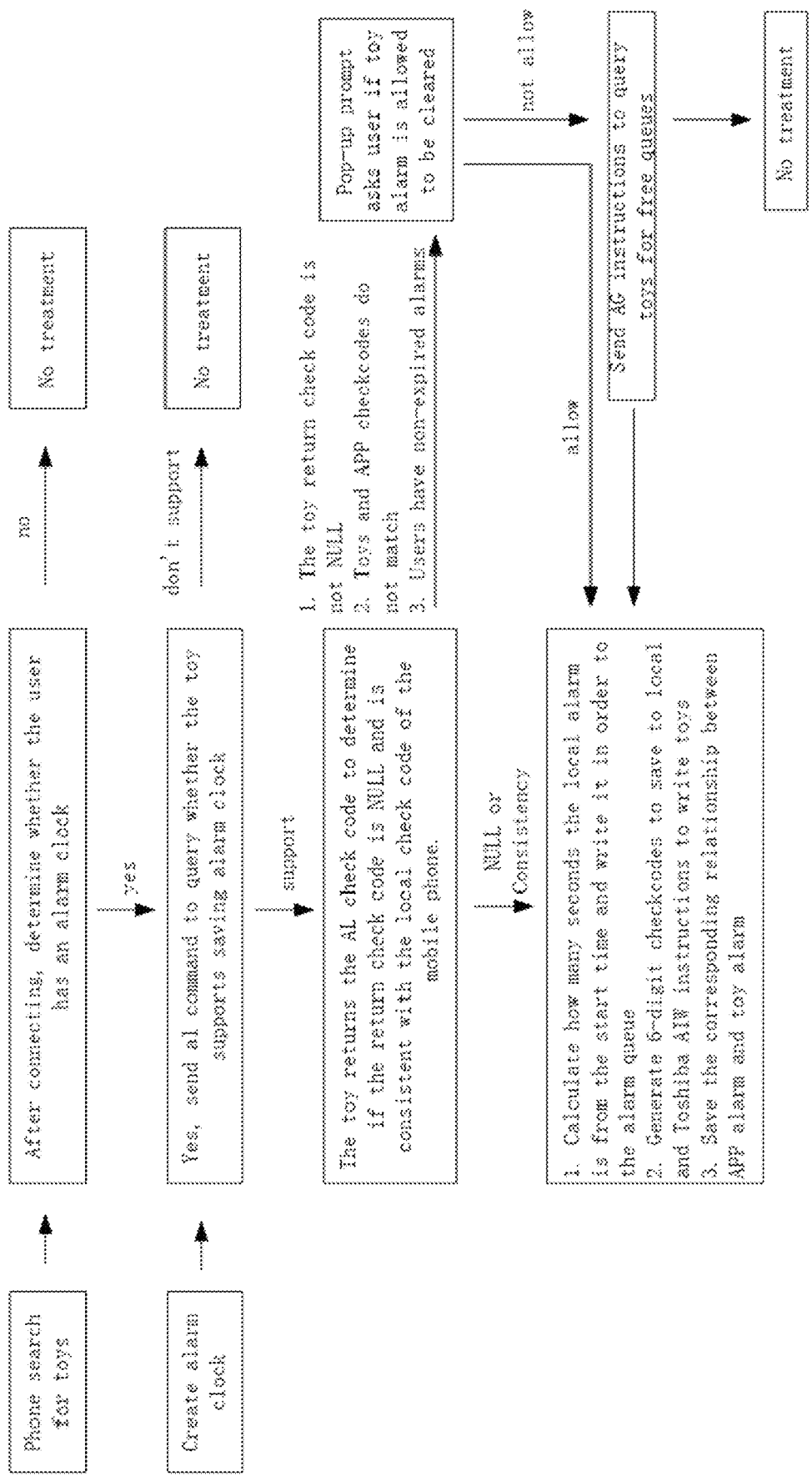
FIG. 5A is a flowchart showing an exemplary process of the present invention.
Figure 5B:
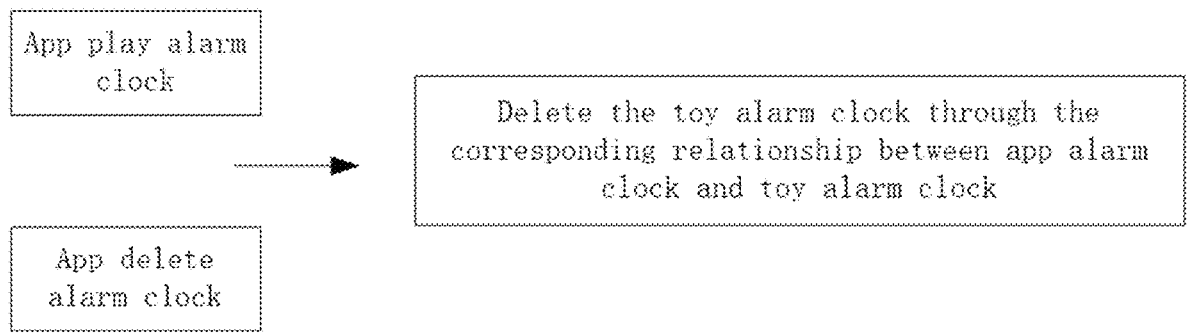
FIG. 5B is a flowchart showing an exemplary process of the present invention.

FIGS. 5A and 5B illustrate an exemplary operation of at least some exemplary embodiments of the exemplary disclosed system, apparatus, and method. As illustrated in FIGS. 5A and 5B, when the exemplary disclosed toy (e.g., viewer accessory 308 and/or model accessory 315) is connected, system 300 may check whether a check code matches an alarm clock written by a current device (e.g., user device 305 and/or model device 310) through an AL instruction. If there is a check code but the check code does not match, system 300 may prompt the user whether or not to clear the data (e.g., based on providing a user interface to prompt the user whether or not to clear the data). In the exemplary disclosed process, the user may choose not to clear the data and may record the operation (e.g., through an AG Command) to query the toy alarm clock, return the value to query whether there is a spare ID (e.g., query the alarm clock of the toy, return the alarm clock set in the toy, return whether or not there is a spare ID to query whether there are more than 10, and may not process if there are more than 10 or any other desired threshold), and write data in the spare alarm clock ID (e.g., do not process if there are more than 10 or any other desired threshold). System 300 may provide a direct write operation if a return value of the instruction is null. System 300 may not perform processing if the check code does not match or the return value is ER. If clearing is allowed, an operation may pass through AC command. The command may clear the original toy alarm clock and directly write the alarm clock data of the current user. If the application check code is null, system 300 may not perform processing.

In at least some exemplary embodiments and as illustrated in FIGS. 5A and 5B, the exemplary disclosed method may include a processing method of written alarm clock data. System 300 may cycle the alarm clock list, sort according to the playing time, and write the first X alarm clock data into the toy (e.g., x<=10, and write AIW). The verification code may be written, and system 300 may record the verification code for processing when the toy is connected (e.g., a 6-bit random number) to obtain the corresponding relationship of the alarm clock. For periodic alarm clock conversion (e.g., from Monday to Sunday), system 300 may convert the data according to the current date. For example if the day is Tuesday and the alarm clock has expired, system 300 may convert the toy alarm clock data of Wednesday, Thursday, Friday, Saturday and Sunday, and then sort the information together with other alarm clocks according to the playback time.

In at least some exemplary embodiments and as illustrated in FIGS. 5A and 5B, when receiving or creating an alarm clock, Ag commands may be used to query the alarm clock data of the accessory. For example if there are less than 10 entries, system 300 may write data in a spare ID. When 10 entries are full, system 300 may query whether the user is allowed to overwrite the data. If overwriting is allowed, system 300 may write 10 entries of data. If overwriting is not allowed, system 300 may close the prompt.

In at least some exemplary embodiments, the exemplary disclosed system may include an alarm control module, comprising computer-executable code stored in non-volatile memory, and an accessory (e.g., viewer accessory 308 or model accessory 315) including an accessory processor and an accessory memory. The alarm control module and the accessory may be configured to control the accessory processor to execute on a first plurality of programming instructions stored by the accessory memory, the first plurality of programming instructions controlling the accessory and including one or more alarm clocks, and when the one or more alarm clocks that are preset in the accessory are activated, drive the accessory. Driving the accessory may include performing one or more predefined sexual stimulation acts to stimulate a human user of the accessory. The accessory may be a sexual stimulation device including a motor or a heater, and the one or more predefined sexual stimulation acts may be at least one selected from the group of vibration, rotation, swinging, inhalation, temperature variation, expansion, suction, contraction, and combinations thereof. The exemplary disclosed system may also include a user device of the human user, the user device including a second processor and a second memory. The alarm control module, the accessory, and the user device may be configured to control the second processor to execute on a second plurality of programming instructions stored by the second memory, the second plurality of programming instructions controlling the user device and including one or more alarm clock information, set the one or more alarm clock information that include one or more alarm clock data for writing into the accessory from the user device, and complete an alarm writing setting of the accessory based on sending the one or more alarm clock information to the accessory that is connected with the user device. The accessory may be connected with the user device via a short-range wireless connection that may be at least one selected from the group of Wi-Fi, Bluetooth, ZigBee, NFC, IrDA, and combinations thereof. The user device may be a mobile phone, a tablet computer, a wearable device, or a smart mobile terminal. The one or more alarm clock information may include drive signals for the one or more predefined sexual stimulation acts that may be associated with each of the one or more alarm clocks. The drive signals for the one or more predefined sexual stimulation acts may include at least one selected from the group of an act duration, an act amplitude, an act frequency, an act intensity when the predefined sexual stimulation act is performed, and combinations thereof. When the user device is disconnected from the accessory, the first plurality of programming instructions may control the accessory. When the one or more alarm clocks sound, based on the completed alarm writing setting, the accessory may perform the one or more predefined sexual stimulation acts based on the drive signals associated with each of the one or more alarm clocks, so as to stimulate the human user. The one or more alarm clock information may include one or more local alarm clocks that may be preset in the user device, the one or more local alarm clocks corresponding to the one or more alarm clocks written into the accessory. The second plurality of programming instructions may be configured to control the user device, and based on the control the user device performing setting the correspondence between the one or more local alarm clocks and the one or more alarm clocks written into the accessory, and associating one or more control patterns for each of the one or more local alarm clocks. The one or more control patterns may include a series of signals for driving the accessory to perform at least one selected from the group of continuously different amplitudes, continuously different frequencies, different intensities of the one or more predefined sexual stimulation acts, and combinations thereof. When the user device is connected to the accessory, the first plurality of programming instructions and the second plurality of programming instructions may be configured to send the series of signals corresponding to the one or more control patterns to the accessory when the one or more local alarm clocks in the user device activate, and drive the accessory to perform at least one selected from the group of continuously different amplitudes, continuously different frequencies, different intensities of the one or more predefined sexual stimulation acts, and combinations thereof. The one or more alarm clock information may include at least one selected from the group of a ring duration of the one or more alarm clocks, a number of alarm repeats, an interval time of the alarm loop, and combinations thereof.

In at least some exemplary embodiments, the exemplary disclosed method may include providing a sexual stimulation device (e.g., viewer accessory 308 or model accessory 315) including an accessory processor and an accessory memory, controlling the accessory processor to execute on a first plurality of programming instructions stored by the accessory memory, providing a user device (e.g., user device 305 or model device 310) of a human user, the user device including a second processor and a second memory, and the user device communicably connected to the sexual stimulation device, and controlling the second processor to execute on a second plurality of programming instructions stored by the second memory. The exemplary disclosed method may also include presetting one or more alarm clocks in the user device, when the one or more alarm clocks activate, sending one or more control signals from the user device to the sexual stimulation device, and driving the sexual stimulation device, based on the one or more control signals, to perform one or more predefined sexual stimulation acts to stimulate the human user. The user device may be communicably connected to the sexual stimulation device via short-range wireless. The one or more predefined sexual stimulation acts may be at least one selected from the group of vibration, rotation, swinging, inhalation, temperature variation, expansion, suction, contraction, and combinations thereof. The exemplary disclosed method may further include completing an alarm writing setting of the sexual stimulation device based on sending one or more alarm clock information from the user device to the sexual stimulation device. The exemplary disclosed method may also include providing a video stream of the human user to a chat room including the human user and one or more other users when the one or more alarm clocks activate.

In at least some exemplary embodiments, the exemplary disclosed system may include an alarm control module, comprising computer-executable code stored in non-volatile memory, a sexual stimulation device (e.g., viewer accessory 308 or model accessory 315) including an accessory processor and an accessory memory, and a user device (e.g., user device 305 or model device 310) of a human user, the user device wirelessly connected to the sexual stimulation device and including a second processor and a second memory. The alarm control module, the sexual stimulation device, and the user device may be configured to control the accessory processor to execute on a first plurality of programming instructions stored by the accessory memory, the first plurality of programming instructions controlling the sexual stimulation device and including one or more alarm clocks, and when the one or more alarm clocks that are preset in the sexual stimulation device are activated, drive the sexual stimulation device. The alarm control module, the sexual stimulation device, and the user device may also be configured to control the second processor to execute on a second plurality of programming instructions stored by the second memory, the second plurality of programming instructions controlling the user device and including one or more alarm clock information, set the one or more alarm clock information that include one or more alarm clock data for writing into the sexual stimulation device from the user device, and complete an alarm writing setting of the sexual stimulation device based on sending the one or more alarm clock information to the sexual stimulation device. Driving the sexual stimulation device may include performing one or more predefined sexual stimulation acts to stimulate the human user. The one or more alarm clock information may include drive signals for the one or more predefined sexual stimulation acts that are associated with each of the one or more alarm clocks. When the user device is disconnected from the sexual stimulation device, the first plurality of programming instructions may control the sexual stimulation device. When the one or more alarm clocks sound, based on the completed alarm writing setting, the sexual stimulation device may perform the one or more predefined sexual stimulation acts based on the drive signals associated with each of the one or more alarm clocks, so as to stimulate the human user.

The exemplary disclosed system, apparatus, and method may provide an efficient and effective technique for controlling devices such as adult toys using an alarm. For example, the exemplary disclosed system, apparatus, and method may control a device to operate based on a desired schedule. Also for example, the exemplary disclosed system, apparatus, and method may provide an efficient and effective technique for controlling a device such as an adult toy to operate using a desired pattern or other criteria according to a desired schedule (e.g., based on alarms).

In at least some exemplary embodiments, the exemplary disclosed system, apparatus, and method may utilize sophisticated machine learning and/or artificial intelligence techniques to prepare and submit datasets and variables to cloud computing clusters and/or other analytical tools (e.g., predictive analytical tools) which may analyze such data using artificial intelligence neural networks. The exemplary disclosed system may for example include cloud computing clusters performing predictive analysis. For example, the exemplary neural network may include a plurality of input nodes that may be interconnected and/or networked with a plurality of additional and/or other processing nodes to determine a predicted result. Exemplary artificial intelligence processes may include filtering and processing datasets, processing to simplify datasets by statistically eliminating irrelevant, invariant or superfluous variables or creating new variables which are an amalgamation of a set of underlying variables, and/or processing for splitting datasets into train, test and validate datasets using at least a stratified sampling technique. The exemplary disclosed system may utilize prediction algorithms and approach that may include regression models, tree-based approaches, logistic regression, Bayesian methods, deep-learning and neural networks both as a stand-alone and on an ensemble basis, and final prediction may be based on the model/structure which delivers the highest degree of accuracy and stability as judged by implementation against the test and validate datasets.

Figure 6:
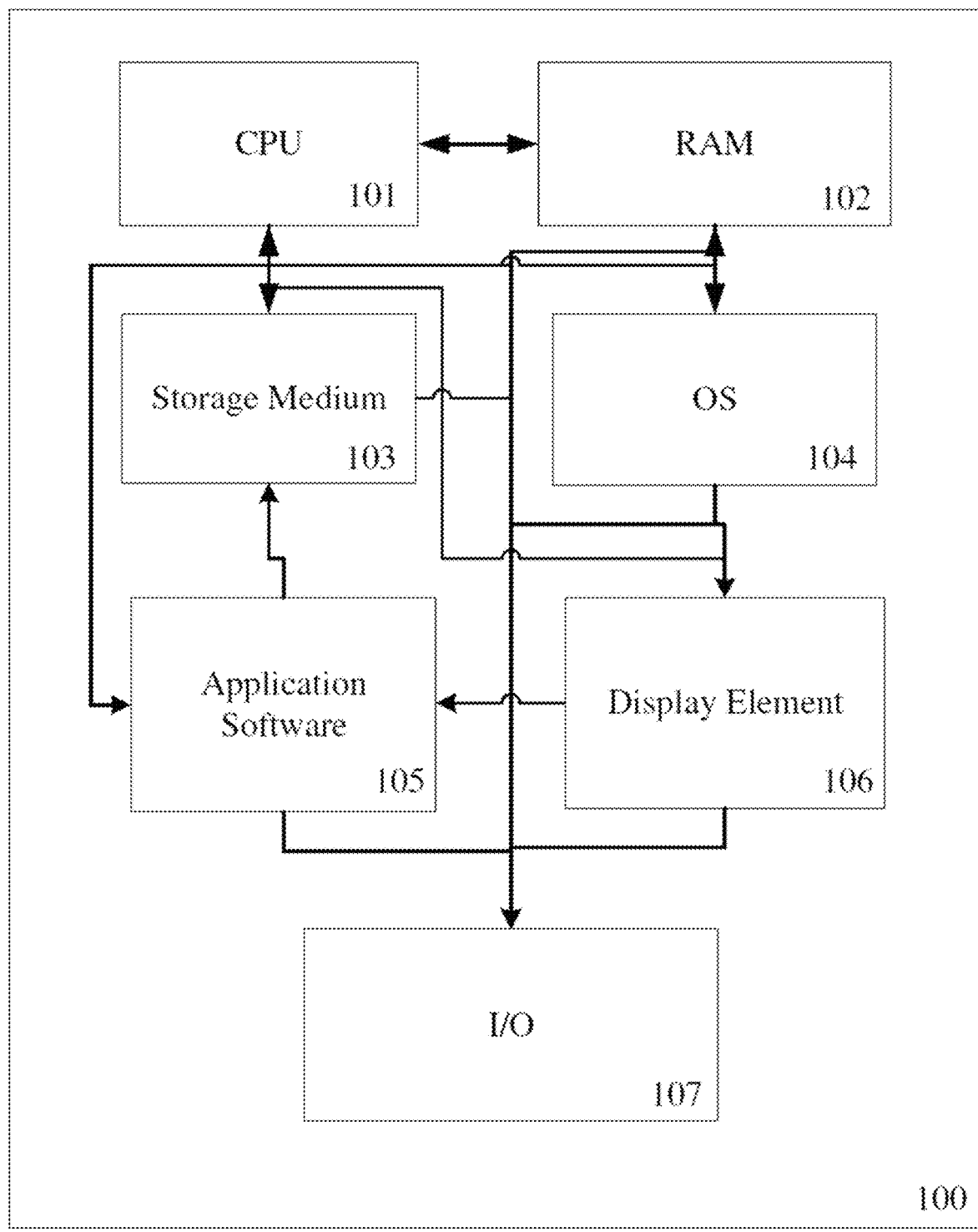
FIG. 6 is a schematic illustration of an exemplary computing device, in accordance with at least some exemplary embodiments of the present disclosure.

An illustrative representation of a computing device appropriate for use with embodiments of the system of the present disclosure is shown in FIG. 6. The computing device 100 can generally be comprised of a Central Processing Unit (CPU, 101), optional further processing units including a graphics processing unit (GPU), a Random Access Memory (RAM, 102), a mother board 103, or alternatively/additionally a storage medium (e.g., hard disk drive, solid state drive, flash memory, cloud storage), an operating system (OS, 104), one or more application software 105, a display element 106, and one or more input/output devices/means 107, including one or more communication interfaces (e.g., RS232, Ethernet, Wifi, Bluetooth, USB). Useful examples include, but are not limited to, personal computers, smart phones, laptops, mobile computing devices, tablet PCs, touch boards, and servers. Multiple computing devices can be operably linked to form a computer network in a manner as to distribute and share one or more resources, such as clustered computing devices and server banks/farms.

Various examples of such general-purpose multi-unit computer networks suitable for embodiments of the disclosure, their typical configuration and many standardized communication links are well known to one skilled in the art, as explained in more detail and illustrated by FIG. 7, which is discussed herein-below.

According to an exemplary embodiment of the present disclosure, data may be transferred to the system, stored by the system and/or transferred by the system to users of the system across local area networks (LANs) (e.g., office networks, home networks) or wide area networks (WANs) (e.g., the Internet). In accordance with the previous embodiment, the system may be comprised of numerous servers communicatively connected across one or more LANs and/or WANs. One of ordinary skill in the art would appreciate that there are numerous manners in which the system could be configured and embodiments of the present disclosure are contemplated for use with any configuration.

In general, the system and methods provided herein may be employed by a user of a computing device whether connected to a network or not. Similarly, some steps of the methods provided herein may be performed by components and modules of the system whether connected or not. While such components/modules are offline, and the data they generated will then be transmitted to the relevant other parts of the system once the offline component/module comes again online with the rest of the network (or a relevant part thereof). According to an embodiment of the present disclosure, some of the applications of the present disclosure may not be accessible when not connected to a network, however a user or a module/component of the system itself may be able to compose data offline from the remainder of the system that will be consumed by the system or its other components when the user/offline system component or module is later connected to the system network.

Figure 7:
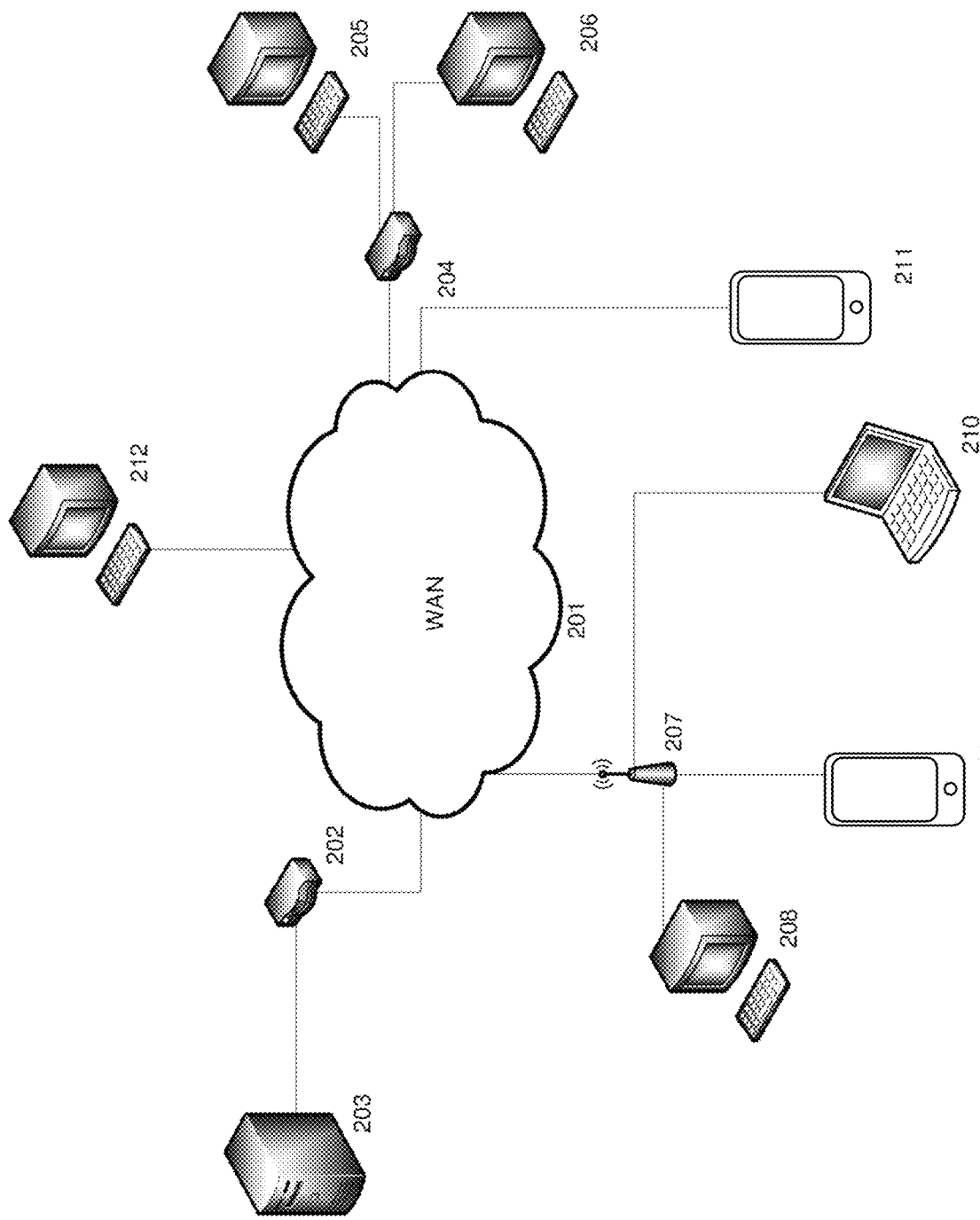
FIG. 7 is a schematic illustration of an exemplary network, in accordance with at least some exemplary embodiments of the present disclosure.

Referring to FIG. 7, a schematic overview of a system in accordance with an embodiment of the present disclosure is shown. The system is comprised of one or more application servers 203 for electronically storing information used by the system. Applications in the server 203 may retrieve and manipulate information in storage devices and exchange information through a WAN 201 (e.g., the Internet). Applications in server 203 may also be used to manipulate information stored remotely and process and analyze data stored remotely across a WAN 201 (e.g., the Internet).

According to an exemplary embodiment, as shown in FIG. 7, exchange of information through the WAN 201 or other network may occur through one or more high speed connections. In some cases, high speed connections may be over-the-air (OTA), passed through networked systems, directly connected to one or more WANs 201 or directed through one or more routers 202. Router(s) 202 are completely optional and other embodiments in accordance with the present disclosure may or may not utilize one or more routers 202. One of ordinary skill in the art would appreciate that there are numerous ways server 203 may connect to WAN 201 for the exchange of information, and embodiments of the present disclosure are contemplated for use with any method for connecting to networks for the purpose of exchanging information. Further, while this application refers to high speed connections, embodiments of the present disclosure may be utilized with connections of any speed.

Components or modules of the system may connect to server 203 via WAN 201 or other network in numerous ways. For instance, a component or module may connect to the system i) through a computing device 212 directly connected to the WAN 201, ii) through a computing device 205, 206 connected to the WAN 201 through a routing device 204, iii) through a computing device 208, 209, 210 connected to a wireless access point 207 or iv) through a computing device 211 via a wireless connection (e.g., CDMA, GMS, 3G, 4G) to the WAN 201. One of ordinary skill in the art will appreciate that there are numerous ways that a component or module may connect to server 203 via WAN 201 or other network, and embodiments of the present disclosure are contemplated for use with any method for connecting to server 203 via WAN 201 or other network. Furthermore, server 203 could be comprised of a personal computing device, such as a smartphone, acting as a host for other computing devices to connect to.

The communications means of the system may be any means for communicating data, including image and video, over one or more networks or to one or more peripheral devices attached to the system, or to a system module or component. Appropriate communications means may include, but are not limited to, wireless connections, wired connections, cellular connections, data port connections, Bluetooth® connections, near field communications (NFC) connections, or any combination thereof. One of ordinary skill in the art will appreciate that there are numerous communications means that may be utilized with embodiments of the present disclosure, and embodiments of the present disclosure are contemplated for use with any communications means.

Traditionally, a computer program includes a finite sequence of computational instructions or program instructions. It will be appreciated that a programmable apparatus or computing device can receive such a computer program and, by processing the computational instructions thereof, produce a technical effect.

A programmable apparatus or computing device includes one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computing device can include any and all suitable combinations of at least one general purpose computer, special-purpose computer, programmable data processing apparatus, processor, processor architecture, and so on. It will be understood that a computing device can include a computer-readable storage medium and that this medium may be internal or external, removable and replaceable, or fixed. It will also be understood that a computing device can include a Basic Input/Output System (BIOS), firmware, an operating system, a database, or the like that can include, interface with, or support the software and hardware described herein.

Embodiments of the system as described herein are not limited to applications involving conventional computer programs or programmable apparatuses that run them. It is contemplated, for example, that embodiments of the disclosure as claimed herein could include an optical computer, quantum computer, analog computer, or the like.

Regardless of the type of computer program or computing device involved, a computer program can be loaded onto a computing device to produce a particular machine that can perform any and all of the depicted functions. This particular machine (or networked configuration thereof) provides a technique for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Illustrative examples of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A data store may be comprised of one or more of a database, file storage system, relational data storage system or any other data system or structure configured to store data. The data store may be a relational database, working in conjunction with a relational database management system (RDBMS) for receiving, processing and storing data. A data store may comprise one or more databases for storing information related to the processing of moving information and estimate information as well one or more databases configured for storage and retrieval of moving information and estimate information.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software components or modules, or as components or modules that employ external routines, code, services, and so forth, or any combination of these. All such implementations are within the scope of the present disclosure. In view of the foregoing, it will be appreciated that elements of the block diagrams and flowchart illustrations support combinations of means for performing the specified functions, combinations of steps for performing the specified functions, program instruction technique for performing the specified functions, and so on.

It will be appreciated that computer program instructions may include computer executable code. A variety of languages for expressing computer program instructions are possible, including without limitation C, C++, Java, JavaScript, assembly language, Lisp, HTML, Perl, and so on. Such languages may include assembly languages, hardware description languages, database programming languages, functional programming languages, imperative programming languages, and so on. In some embodiments, computer program instructions can be stored, compiled, or interpreted to run on a computing device, a programmable data processing apparatus, a heterogeneous combination of processors or processor architectures, and so on. Without limitation, embodiments of the system as described herein can take the form of web-based computer software, which includes client/server software, software-as-a-service, peer-to-peer software, or the like.

In some embodiments, a computing device enables execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. The thread can spawn other threads, which can themselves have assigned priorities associated with them. In some embodiments, a computing device can process these threads based on priority or any other order based on instructions provided in the program code.

Unless explicitly stated or otherwise clear from the context, the verbs "process" and "execute" are used interchangeably to indicate execute, process, interpret, compile, assemble, link, load, any and all combinations of the foregoing, or the like. Therefore, embodiments that process computer program instructions, computer-executable code, or the like can suitably act upon the instructions or code in any and all of the ways just described.

The functions and operations presented herein are not inherently related to any particular computing device or other apparatus. Various general-purpose systems may also be used with programs in accordance with the teachings herein, or it may prove convenient to construct more specialized apparatus to perform the required method steps. The required structure for a variety of these systems will be apparent to those of ordinary skill in the art, along with equivalent variations. In addition, embodiments of the disclosure are not described with reference to any particular programming language. It is appreciated that a variety of programming languages may be used to implement the present teachings as described herein, and any references to specific languages are provided for disclosure of enablement and best mode of embodiments of the disclosure. Embodiments of the disclosure are well suited to a wide variety of computer network systems over numerous topologies. Within this field, the configuration and management of large networks include storage devices and computing devices that are communicatively coupled to dissimilar computing and storage devices over a network, such as the Internet, also referred to as "web" or "world wide web".

Throughout this disclosure and elsewhere, block diagrams and flowchart illustrations depict methods, apparatuses (e.g., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on—any and all of which may be generally referred to herein as a "component", "module," or "system."

While the foregoing drawings and description set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

The functions, systems and methods herein described could be utilized and presented in a multitude of languages. Individual systems may be presented in one or more languages and the language may be changed with ease at any point in the process or methods described above. One of ordinary skill in the art would appreciate that there are numerous languages the system could be provided in, and embodiments of the present disclosure are contemplated for use with any language.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

It will be apparent to those skilled in the art that various modifications and variations can be made to the disclosed system and method. Other embodiments will be apparent to those skilled in the art from consideration of the specification and practice of the disclosed method and apparatus. It is intended that the specification and examples be considered as exemplary only, with a true scope being indicated by the following claims.

What is claimed is:

1. A system, comprising:
  an alarm control module, comprising computer-executable code stored in non-volatile memory;
  an accessory including an accessory processor and an accessory memory; and
  a user device of a human user, the user device including a second processor and a second memory;
  wherein the alarm control module, the second processor of the user device, and the accessory processor of the accessory are configured to:

control the second processor to execute on a second plurality of programming instructions stored by the second memory, the second plurality of programming instructions controlling the user device and including one or more alarm clock information;

set the one or more alarm clock information, which includes one or more alarm clock data, for writing into the accessory from the user device;

complete an alarm writing setting of the accessory, which includes sending the one or more alarm clock information to the accessory from the user device;

wherein the one or more alarm clock information includes one or more local alarm clocks that are preset in the user device, the one or more local alarm clocks corresponding to one or more alarm clocks of the one or more alarm clock data written for writing into the accessory;

control the accessory processor to execute on a first plurality of programming instructions stored by the accessory memory, the first plurality of programming instructions controlling the accessory, which includes the one or more local alarm clocks that are preset in the user device; and when the one or more local alarm clocks that are present in the user device are activated, drive the accessory;

wherein driving the accessory includes performing one or more predefined sexual stimulation acts to stimulate the human user.

2. The system of claim 1, wherein the accessory is a sexual stimulation device including a motor or a heater, and the one or more predefined sexual stimulation acts is at least one selected from the group of vibration, rotation, swinging, inhalation, temperature variation, expansion, suction, contraction, and combinations thereof.

3. The system of claim 1, wherein the accessory is connected with the user device via a short-range wireless connection.

4. The system of claim 1, wherein the user device is a mobile phone, a tablet computer, a wearable device, or a smart mobile terminal.

5. The system of claim 1, wherein the one or more alarm clock information includes drive signals for the one or more predefined sexual stimulation acts, which are associated with each of the one or more alarm clocks.

6. The system of claim 5, wherein the drive signals for the one or more predefined sexual stimulation acts include at least one selected from the group of an act duration, an act amplitude, an act frequency, an act intensity when the one or more predefined sexual stimulation acts is performed, and combinations thereof.

7. The system of claim 5, wherein:
when the user device of the human user is disconnected from the accessory, the first plurality of programming instructions control the accessory; and
when the one or more alarm clocks are activated, after completing the alarm writing setting of the accessory, the accessory performs the one or more predefined sexual stimulation acts based on the drive signals associated with each of the one or more alarm clocks, so as to stimulate the human user.

8. The system of claim 1, wherein the second plurality of programming instructions are configured to control the user device, and based on the control, the user device performing:
associating one or more control patterns with each of the one or more local alarm clocks;
wherein the one or more control patterns include a series of signals for driving the accessory to perform at least one selected from the group of continuously different amplitudes, continuously different frequencies, different intensities of the one or more predefined sexual stimulation acts, and combinations thereof.

9. The system of claim 8, wherein the user device and the accessory are communicably connected, and when the user device is connected to the accessory, the first plurality of programming instructions and the second plurality of programming instructions are configured to:
send the series of signals to the accessory when the one or more local alarm clocks in the user device activate; and
drive the accessory to perform at least one selected from the group of continuously different amplitudes, continuously different frequencies, different intensities of the one or more predefined sexual stimulation acts, and combinations thereof.

10. The system of claim 1, wherein the one or more alarm clock information includes at least one selected from the group of a ring duration of the one or more alarm clocks, a number of alarm repeats, an interval time of an alarm loop, and combinations thereof.

11. A method, comprising:
connecting a sexual stimulation device and a user device of a human user, the sexual stimulation device including an accessory processor and an accessory memory, the user device including a second processor and a second memory, and the user device communicably connected to the sexual stimulation device;
controlling the accessory processor to execute on a first plurality of programming instructions stored by the accessory memory;
controlling the second processor to execute on a second plurality of programming instructions stored by the second memory, the second plurality of programming instructions controlling the user device and including one or more alarm clock information;
setting the one or more alarm clock information, which includes one or more alarm clock data, for writing into the sexual stimulation device from the user device;
completing an alarm writing setting of the sexual stimulation device, which includes sending the one or more alarm clock information to the sexual stimulation device from the user device;
wherein the one or more alarm clock information includes one or more local alarm clocks that are preset in the user device, the one or more local alarm clocks corresponding to one or more alarm clocks of the one or more alarm clock data for writing into the sexual stimulation device;
presetting the one or more local alarm clocks in the user device;
wherein when the one or more local alarm clocks activates following the presetting, sending one or more control signals from the user device to the sexual stimulation device; and
driving the sexual stimulation device, based on the one or more control signals, to perform one or more predefined sexual stimulation acts to stimulate the human user.

12. The method of claim 11, wherein the user device is communicably connected to the sexual stimulation device via short-range wireless.

13. The method of claim 11, wherein the one or more predefined sexual stimulation acts is at least one selected from the group of vibration, rotation, swinging, inhalation, temperature variation, expansion, suction, contraction, and combinations thereof.

14. The method of claim 11, further comprising providing a video stream of the human user to a chat room including the human user and one or more other users when the one or more alarm clocks activate.

15. An apparatus, comprising:
a processor; and
an alarm control module, comprising computer-executable code stored in non-volatile memory;
wherein the processor is configured to:
connect a sexual stimulation device and a user device of a human user, the sexual stimulation device including an accessory processor and an accessory memory, the user device including a second processor and a second memory, and the user device communicably connected to the sexual stimulation device;
control the second processor to execute on a second plurality of programming instructions stored by the second memory, the second plurality of programming instructions controlling the user device and including one or more alarm clock information;
set the one or more alarm clock information, which includes one or more alarm clock data, for writing into the sexual stimulation device from the user device;
complete an alarm writing setting of the sexual stimulation device, which includes sending the one or more alarm clock information to the sexual stimulation device from the user device;
wherein the one or more alarm clock information includes one or more local alarm clocks that are preset in the user device, the one or more local alarm clocks corresponding to one or more alarm clocks of the one or more alarm clock data for writing into the sexual stimulation device;
control the accessory processor to execute on a first plurality of programming instructions stored by the accessory memory, the first plurality of programming instructions controlling the sexual stimulation device, which includes the one or more alarm clocks for writing into the sexual stimulation device; and
when the one or more local alarm clocks that are present in the user device are activated, drive the sexual stimulation device;
wherein driving the sexual stimulation device includes performing one or more predefined sexual stimulation acts to stimulate the human user.

16. The apparatus of claim 15, wherein the one or more alarm clock information includes drive signals for the one or more predefined sexual stimulation acts, which are associated with each of the one or more alarm clocks.

17. The apparatus of claim 16, wherein:
the user device and the sexual stimulation device are communicably connected, and when the user device is disconnected from the sexual stimulation device, the first plurality of programming instructions control the sexual stimulation device; and
when the one or more alarm clocks are activated, after completing the alarm writing setting of the sexual stimulation device, the sexual stimulation device performs the one or more predefined sexual stimulation acts based on the drive signals associated with each of the one or more alarm clocks, so as to stimulate the human user.

* * * * *